(12) United States Patent
Kadziauskas et al.

(10) Patent No.: US 8,197,436 B2
(45) Date of Patent: Jun. 12, 2012

(54) MICRO-BURST ULTRASONIC POWER DELIVERY

(75) Inventors: Kenneth E. Kadziauskas, Coto de Caza, CA (US); Paul W. Rockley, Corona Del Mar, CA (US); James W. Staggs, Laguna Niguel, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 0 days.

(21) Appl. No.: 12/979,924

(22) Filed: Dec. 28, 2010

(65) Prior Publication Data

US 2011/0160646 A1    Jun. 30, 2011

Related U.S. Application Data

(63) Continuation of application No. 11/560,328, filed on Nov. 15, 2006, now Pat. No. 7,857,783, which is a continuation of application No. 10/853,863, filed on May 25, 2004, now Pat. No. 7,485,106, which is a continuation of application No. 10/085,508, filed on Feb. 26, 2002, now Pat. No. 6,780,165, which is a continuation-in-part of application No. 09/764,814, filed on Jan. 16, 2001, now Pat. No. 6,629,948, which is a continuation-in-part of application No. 09/298,669, filed on Apr. 23, 1999, now Pat. No. 6,394,974, which is a continuation-in-part of application No. 09/206,452, filed on Dec. 7, 1998, now abandoned, which is a continuation of application No. 08/787,229, filed on Jan. 22, 1997, now Pat. No. 5,852,794.

(51) Int. Cl.
  *A61B 17/20* (2006.01)

(52) U.S. Cl. ........................................ 604/22

(58) Field of Classification Search ................ 604/22, 604/65, 118; 606/128, 169, 107, 170, 171; 600/437, 439, 471

See application file for complete search history.

(56) References Cited

U.S. PATENT DOCUMENTS

| | | | |
|---|---|---|---|
| 2,434,480 A | 1/1948 | Anderson | |
| 3,857,387 A | 12/1974 | Shock | |
| 3,941,122 A | 3/1976 | Jones | |
| 4,184,510 A | 1/1980 | Murry et al. | |

(Continued)

FOREIGN PATENT DOCUMENTS

CA    2242328 A1    5/1998

(Continued)

OTHER PUBLICATIONS

Devine M.D., et al., "How to Set the Dials," Phacoemulsification Surgery, 1991, pp. 7-28.

(Continued)

*Primary Examiner* — Manuel Mendez
(74) *Attorney, Agent, or Firm* — Abbott Medical Optics Inc.

(57) ABSTRACT

Phacoemulsification apparatus includes a phacoemulsification handpiece having a needle and an electrical system for ultrasonically vibrating said needle along with a power source for providing pulsed electrical power to the handpiece electrical system. Irrigation fluid is provided to the handpiece needle and aspirating fluid is removed from the handpiece needle. A determination of a voltage current phase relationship of the provided electrical power is made and in response thereto a control system varies a power level duty cycle provided to the handpiece electrical system from the power source and/or modify the aspiration flow rate. In addition, a separate input enables manual control of pulse amplitude. The control system provides a pulsed electrical power of less than 20 millisecond pulse duration.

6 Claims, 12 Drawing Sheets

U.S. PATENT DOCUMENTS

| | | |
|---|---|---|
| 4,343,111 A | 8/1982 | Inoue |
| 4,736,130 A | 4/1988 | Puskas |
| 4,808,948 A | 2/1989 | Patel et al. |
| 4,827,911 A | 5/1989 | Broadwin et al. |
| 4,952,834 A | 8/1990 | Okada |
| 4,954,960 A | 9/1990 | Lo et al. |
| 4,970,656 A | 11/1990 | Lo et al. |
| 4,983,901 A | 1/1991 | Lehmer |
| 5,001,649 A | 3/1991 | Lo et al. |
| 5,091,656 A | 2/1992 | Gahn |
| 5,209,221 A | 5/1993 | Riedlinger |
| 5,213,569 A | 5/1993 | Davis |
| 5,242,404 A | 9/1993 | Conley et al. |
| 5,249,121 A | 9/1993 | Baum et al. |
| 5,268,624 A | 12/1993 | Zanger |
| 5,279,547 A | 1/1994 | Costin |
| 5,318,563 A | 6/1994 | Malis et al. |
| 5,331,951 A | 7/1994 | Kepley |
| 5,342,293 A | 8/1994 | Zanger |
| 5,370,602 A | 12/1994 | Kepley |
| 5,388,569 A | 2/1995 | Kepley |
| 5,403,307 A | 4/1995 | Zelman |
| 5,405,614 A | 4/1995 | D'Angelo et al. |
| 5,406,503 A | 4/1995 | Williams, Jr. et al. |
| 5,417,246 A | 5/1995 | Perkins et al. |
| 5,431,664 A | 7/1995 | Ureche et al. |
| 5,453,087 A | 9/1995 | Malinowski |
| 5,520,633 A | 5/1996 | Costin |
| 5,534,741 A | 7/1996 | Smith |
| 5,547,459 A | 8/1996 | Kaufman et al. |
| 5,582,578 A | 12/1996 | Zhong et al. |
| 5,591,127 A | 1/1997 | Barwick, Jr. et al. |
| 5,700,240 A | 12/1997 | Barwick, Jr. et al. |
| 5,733,256 A | 3/1998 | Costin |
| 5,738,677 A | 4/1998 | Colvard et al. |
| 5,766,146 A | 6/1998 | Barwick, Jr. |
| 5,797,494 A | 8/1998 | Balling et al. |
| 5,800,365 A | 9/1998 | Zhong et al. |
| 5,808,396 A | 9/1998 | Boukhny |
| 5,836,959 A | 11/1998 | Seibel et al. |
| 5,852,794 A | 12/1998 | Staggs |
| 5,873,885 A | 2/1999 | Weidenbenner |
| 5,938,677 A | 8/1999 | Boukhny et al. |
| 5,979,494 A | 11/1999 | Perkins et al. |
| 5,984,882 A | 11/1999 | Rosenschein et al. |
| 5,997,528 A | 12/1999 | Bisch et al. |
| 6,010,496 A | 1/2000 | Appelbaum et al. |
| 6,083,193 A | 7/2000 | Kadziauskas et al. |
| 6,086,598 A | 7/2000 | Appelbaum et al. |
| 6,117,126 A | 9/2000 | Appelbaum et al. |
| 6,155,975 A | 12/2000 | Urich et al. |
| 6,161,545 A | 12/2000 | Chow |
| 6,175,180 B1 | 1/2001 | Angelini et al. |
| 6,193,683 B1 | 2/2001 | Ludin et al. |
| 6,203,516 B1 | 3/2001 | Kepley |
| 6,251,113 B1 | 6/2001 | Appelbaum et al. |
| 6,261,297 B1 | 7/2001 | Kadziauskas et al. |
| 6,319,220 B1 | 11/2001 | Bylsma |
| 6,391,020 B1 | 5/2002 | Kurtz et al. |
| 6,391,042 B1 | 5/2002 | Cimino |
| 6,394,974 B1 | 5/2002 | Kadziauskas et al. |
| 6,425,883 B1 | 7/2002 | Urich et al. |
| 6,428,531 B1 | 8/2002 | Visuri et al. |
| 6,443,900 B2 | 9/2002 | Adachi et al. |
| 6,452,120 B1 | 9/2002 | Chen |
| 6,452,123 B1 | 9/2002 | Chen |
| 6,452,883 B2 | 9/2002 | Chan |
| 6,487,447 B1 | 11/2002 | Weimann et al. |
| 6,506,176 B1 | 1/2003 | Mittelstein et al. |
| 6,589,204 B1 | 7/2003 | Sussman et al. |
| 6,610,052 B2 | 8/2003 | Furumoto |
| 6,629,948 B2 | 10/2003 | Rockley et al. |
| 6,699,212 B1 | 3/2004 | Kadziauskas et al. |
| 6,726,679 B1 | 4/2004 | Dick et al. |
| 6,733,491 B2 | 5/2004 | Kadziauskas et al. |
| 6,780,165 B2 | 8/2004 | Kadziauskas et al. |
| 6,808,396 B2 | 10/2004 | Kawaguchi et al. |
| 6,884,252 B1 | 4/2005 | Urich et al. |
| 6,890,332 B2 | 5/2005 | Truckai et al. |
| 6,896,674 B1 | 5/2005 | Woloszko et al. |
| 6,908,472 B2 | 6/2005 | Wiener et al. |
| 6,939,317 B2 | 9/2005 | Zacharias |
| 6,962,583 B2 | 11/2005 | Kadziauskas et al. |
| 7,077,820 B1 | 7/2006 | Kadziauskas et al. |
| 7,169,123 B2 | 1/2007 | Kadziauskas et al. |
| 7,193,521 B2 | 3/2007 | Moberg et al. |
| 7,316,664 B2 | 1/2008 | Kadziauskas et al. |
| 7,485,106 B2 | 2/2009 | Kadziauskas et al. |
| 2001/0003155 A1 | 6/2001 | Rockley et al. |
| 2001/0003295 A1 | 6/2001 | Langlotz et al. |
| 2001/0003385 A1 | 6/2001 | Ise |
| 2002/0052600 A1 | 5/2002 | Davison et al. |
| 2002/0072741 A1 | 6/2002 | Sliwa et al. |
| 2002/0082793 A1 | 6/2002 | Kadziauskas et al. |
| 2004/0092921 A1 | 5/2004 | Kadziauskas et al. |
| 2004/0092922 A1 | 5/2004 | Kadziauskas et al. |
| 2004/0193182 A1 | 9/2004 | Yaguchi et al. |
| 2005/0054971 A1 | 3/2005 | Steen et al. |
| 2005/0209560 A1 | 9/2005 | Boukhny et al. |
| 2005/0209621 A1 | 9/2005 | Gordon et al. |
| 2005/0288665 A1 | 12/2005 | Woloszko |
| 2006/0149301 A1 | 7/2006 | Claus |
| 2006/0195077 A1 | 8/2006 | Kadziauskas et al. |
| 2006/0264809 A1 | 11/2006 | Hansmann et al. |
| 2007/0056596 A1 | 3/2007 | Fanney et al. |
| 2007/0073214 A1 | 3/2007 | Dacquay et al. |
| 2007/0078379 A1 | 4/2007 | Boukhny et al. |

FOREIGN PATENT DOCUMENTS

| | | |
|---|---|---|
| DE | 19940712 A | 3/2001 |
| EP | 270819 A2 | 6/1988 |
| EP | 270819 A3 | 1/1989 |
| EP | 336620 A2 | 10/1989 |
| EP | 336620 B1 | 12/1993 |
| EP | 1351631 A1 | 10/2003 |
| EP | 1537840 A1 | 6/2005 |
| JP | 2204337 A2 | 8/1990 |
| JP | 5038343 A2 | 2/1993 |
| JP | 6183762 A2 | 7/1994 |
| JP | 6189972 A2 | 7/1994 |
| JP | 9313496 A2 | 12/1997 |
| JP | 2001161740 A2 | 6/2001 |
| JP | 2002087836 A2 | 3/2002 |
| JP | 2002233534 A2 | 8/2002 |
| WO | WO9520374 A1 | 8/1995 |
| WO | WO9808442 A1 | 3/1998 |
| WO | WO0051508 A1 | 9/2000 |
| WO | WO0064388 A1 | 11/2000 |
| WO | WO0113838 A1 | 3/2001 |
| WO | WO02056806 A1 | 7/2002 |
| WO | WO2005092023 A2 | 10/2005 |

OTHER PUBLICATIONS

"Ocusystem Operation Manual, May 1995, 79 pages,".

"Pulsar cuts phaco time, boots efficiency in cataract removal; Ophthalmology Times: Aug. 15, 1986; 1 page, 11 (16), Harcourt Brace Jovanovich, Inc,".

Taylor W.F.,et al., "Intraoperative Troubleshooting of an Advanced Phacoemulsification System,"The Surgial Technologist, 1985, vol. 17 (2), pp. 11-14.

Phacoemulsification System, The Surgical Technologist, 1985, vol. 17 (2), pp. 11-14.

MICRO-BURST ULTRASONIC POWER DELIVERY

This application is a continuation of U.S. patent application Ser. No. 11/560,328, filed Nov. 15, 2006, now U.S. Pat. No. 7,857,783, issued Dec. 28, 2010, which is a continuation of U.S. patent application Ser. No. 10/853,863 filed May 25, 2004, now U.S. Pat. No. 7,485,106, issued Feb. 3, 2009, which is a continuation of U.S. patent application Ser. No. 10/085,508 filed Feb. 26, 2002, now U.S. Pat. No. 6,780,165, issued Aug. 24, 2004, which is a continuation-in-part of U.S. patent application Ser. No. 09/764,814 filed Jan. 16, 2001, now U.S. Pat. No. 6,629,948, issued Oct. 7, 2003, which is a continuation-in-part of U.S. patent application Ser. No. 09/298,669 filed Apr. 23, 1999, now U.S. Pat. No. 6,394,974, issued May 28, 2002, which is a continuation-in-part of U.S. patent application Ser. No. 09/206,452 filed Dec. 7, 1998, now abandoned, which is a continuation of U.S. patent application Ser. No. 08/787,229, filed Jan. 22, 1997, now U.S. Pat. No. 5,852,794, issued Dec. 22, 1998. Each application listed hereinabove are hereby incorporated by reference in their entirety.

The present invention is generally directed to a method and apparatus for controlling the flow of fluid from a source to a patient and removal of fluids from the patient through a phacoemulsification handpiece as well as controlling power provided to the phacoemulsification handpiece.

The flow of fluid to and from a patient through a fluid infusion or extraction system and power control to a phacoemulsification handpiece is critical to the procedure being performed.

A number of medically recognized techniques has been utilized for lens removal and among these, a popular technique is phacoemulsification, irrigation and aspiration. This method includes the making of a corneal incision, and the insertion of a handheld surgical implement which includes a needle which is ultrasonically driven in order to emulsify the eye lens. Simultaneously with this emulsification, a fluid is inserted for irrigation of the emulsified lens and a vacuum provided for aspiration of the emulsified lens and inserted fluids.

Currently available phacoemulsification systems include a variable speed peristaltic pump, a vacuum sensor, an adjustable source of ultrasonic power and a programmable microprocessor with operator-selected presets for controlling aspiration rate, vacuum and ultrasonic power levels.

Many surgical instruments and controls in use today linearly control the vacuum or linearly control the flow of aspiration fluid. This feature allows the surgeon to precisely "dispense" or control the "speed" at which he/she employs, either the vacuum or the flow, but not both. However, there often are times during surgery when the precise control of one of the variables (vacuum, aspiration rate, or ultrasonic power) is desired over the other. The experienced user, understanding the relationship between the vacuum and the flow, may manually adjust the preset variable appropriately at the console in order to obtain an acceptable performance. However, if this adjustment is overlooked, then the combination of both high vacuum and high flow can cause undesirable fluidic surges at the surgical site with possible damage inflicted on the patient.

It should be apparent that the control of handheld surgical instruments for use in phaco surgery is complex. Phacoemulsifier apparatus typically comprises a cabinet, including a power supply, peristaltic pump, electronic and associated hardware, and a connected, multi-function and handheld surgical implement, or handpiece, including a hollow slender-like needle tube as hereinabove described, in order to perform the phacoemulsification of the cataractous lens.

It should be appreciated that a surgeon utilizing the handheld implement to perform the functions hereinabove described requires easy and accessible control of these functions, as well as the ability to selectively shift or switch between at least some of the functions (for example, irrigation and irrigation plus aspiration) as may arise during phacoemulsification surgery.

In view of the difficulty with adjusting cabinet-mounted controls, while operating an associated handheld medical implement, control systems have been developed such as described in U.S. Pat. No. 4,983,901. This patent is to be incorporated entirely into the present application, including all specification and drawings for the purpose of providing a background to the complex controls required in phacoemulsification surgery and for describing apparatus which may be utilized or modified for use with the method of the present invention.

To further illustrate the complexity of the control system, reference is also made to U.S. Pat. No. 5,268,624. This patent application is to be incorporated in the present application by this specific reference thereto, including all specifications and drawings for the purpose of further describing the state-of-the-art in the field of this invention.

It should thus be apparent, in view of the complex nature of the control system of fluids and ultrasonic power in the case of phacoemulsification procedures, that it is desirable for a surgeon to have a system which is programmable to serve both the needs of the surgical procedure and particular techniques of the surgeon, which may differ depending on the experience and ability of the surgeon.

The present invention more specifically relates to power control to a phacoemulsification handpiece based on the determination of the phase angle between voltage applied to a handpiece piezoelectric transducer and the current drawn by the piezoelectric transducer and/or the amplitude of power pulses provided to the handpiece.

Phacoemulsification systems typically include a handpiece having an ultrasonically vibrated hollow needle and an electronic control therefor.

As is well known in the art, the phacoemulsification handpiece is interconnected with a control console by an electric cable for powering and controlling the piezoelectric transducer and tubing for providing irrigation fluid to the eye and withdrawing aspiration fluid from an eye through the handpiece.

The hollow needle of the handpiece is typically driven or excited along its longitudinal axis by the piezoelectric effect in crystals created by an AC voltage applied thereto. The motion of the driven crystal is amplified by a mechanically resonant system within the handpiece, such that the motion of the needle connected thereto is directly dependent upon the frequency at which the crystal is driven, with a maximum motion occurring at a resonant frequency.

The resonant frequency is dependent, in part upon the mass of the needle interconnected therewith, which is vibrated by the crystal.

For pure capacitive circuits, there is a 90 degree phase angle between a sine wave representing the voltage applied to the handpiece and the resultant current into the handpiece. This is expressed by the angle equaling −90 degrees. For a purely inductive circuit, the phase angle equals +90 degrees and, of course, for purely resistive circuits=0.

A typical range of frequency used for phacoemulsification handpiece is between about 30 kHz to about 50 kHz. A frequency window exists for each phacoemulsification handpiece that can be characterized by the handpiece impedance and phase.

This frequency window is bounded by an upper frequency and a lower cutoff frequency. The center of this window is typically defined as the point where the handpiece electrical phase reaches a maximum value.

At frequencies outside of this window, the electrical phase of the handpiece is equal to −90 degrees.

Handpiece power transfer efficiency is given by the formula (V*I)(COS). This means that the most efficient handpiece operating point occurs when the phase is closest to 0 degrees.

In order to maintain optimum handpiece power transfer efficiency, it is important to control the frequency to achieve a phase value as close to zero degrees as possible.

This goal is complicated by the fact that the phase angle of the ultrasonic handpiece is also dependent on the loading of the transducer which occurs through the mechanically resonant system which includes the needle.

That is, contact by the needle with tissue and fluids within the eye create a load on the piezoelectric crystals with concomitant change in the operating phase angle.

Consequently, it is important to determine and measure the phase angles at all times during operation of the handpiece in order to adjust the driving circuitry to achieve an optimum phase angle in order to effect constant energy transfer into the tissue by the phaco handpiece, regardless of loading effects.

Thus, it is important to provide automatic tuning of the handpiece during its use in phacoemulsification tissue and withdrawing same from an eye. This auto tuning is accomplished by monitoring the handpiece electrical signals and adjusting the frequency to maintain consistency with selected parameters.

In any event, control circuitry for phacoemulsification handpiece can include circuitry for measuring the phase between the voltage and the current, typically identified as a phase detector. However, problems arise in the measurement of the phase shift without dependence on the operating frequency of the phacoemulsification handpiece. That is, because, as hereinabove noted, the phase shift is dependent on the operating frequency of the handpiece and time delay in the measurement thereof requires complex calibration circuitry in order to compensate to provide for responsive tuning of the handpiece.

Phase detection is the process of applying two electrical periodic signals of similar frequency into an electrical circuit that generates a voltage proportional to the time (phase) difference between the two signals.

This voltage generated by the phase detector is then usually time averaged either by an electronic circuit or sampled by an A/D converter and then averaged digitally.

The averaged signal can be read by a conventional voltage meter or used by a microprocessor as date for processing. The averaging also helps to reject electrical noise.

As was described earlier, the output of a phase detector is proportional to the difference in time (of occurrence) to two signals. By definition, this means that while the electrical output of a conventional phase detector is a function of the signal phase, it is also directly proportional to the frequency of use. This means that the frequency of use must be known and compensated for when reading the phase detector output in order to derive quantified phase values. While, as hereinabove noted, a calibration circuit can account for the variation of the frequency, such a circuit is usually very complex and may require the use of a microcontroller. In addition, neither of these approaches account for the drift in performance over time which is typical of phacoemulsification handpieces.

This problem was recognized in U.S. Pat. No. 5,431,664, which provided a solution by using the admittance of the transducers as the tuning parameter rather than the phase-angle. The necessary circuitry is, of course, complicated and accordingly there is still a continuing need for a method for determining real time electrical phase for a piezoelectric phacoemulsification handpiece which is consistent over the entire handpiece range of operation which does not require further calibration circuitry for the controller.

The ultrasonically driven needle in a phaco handpiece becomes warm during use and such generated heat is for the most part dissipated by the irrigation/aspiration fluids passing through the needle. However, care must be taken to avoid overheating of eye tissue during phacoemulsification.

Interrupted power pulse methods have been developed in order to drive the needle with reduced heating to avoid overheating and burning of tissue. The present invention improves this power pulse method.

SUMMARY OF THE INVENTION

In accordance with the present invention, phacoemulsification apparatus generally includes a phacoemulsification handpiece having a needle and an electrical means for ultrasonically vibrating the needle. The power source provides a means for supplying pulsed electrical power to the handpiece electrical means and a means for providing irrigation to the eye and aspirating fluid from the handpiece needle is also incorporated in the present invention.

Input means is provided for enabling a surgeon to select an amplitude of the electrical pulse. Control means is provided for controlling a pulse duty cycle. In that regard, a controlled off duty cycle is established by the control means in order to ensure heat dissipation before a subsequent pulse is activated. Preferably the control means provides a pulse of less than 20 milliseconds or a repetition rate of between about 25 and about 2000 pulses per second.

In another embodiment of the present invention, a means for determining the voltage current phase relationship of the provided electrical power is provided.

In this embodiment, the control means is responsive to both the pulse amplitude and the determined voltage current phase relationship for varying a pulse duty cycle of the power supply to the handpiece.

The means for determining the voltage current phase relationship generally includes the means for obtaining an AC voltage signal corresponding to the operating AC voltage of a piezoelectric handpiece and means for obtaining an AC current signal corresponding to the operating AC current of the piezoelectric handpiece.

Means are provided for determining the onset of a current cycle from the AC current signal and means are also provided for producing a voltage ($V_I$) corresponding to a time necessary for the AC current to reach a maximum value after onset of the current cycle.

Additionally, means are provided for producing a voltage ($V_v$) corresponding to a time necessary for the AC voltage to reach a maximum value after onset of the current cycle.

An A/D converter provides a means for comparing ($V_v$) and ($V_I$) to determine the phase relationship between the voltage and current of the piezoelectric phacoemulsification handpiece and generating a phase signal ($S_p$) corresponding thereto, the phase signal being frequency independent.

A method in accordance with the present invention for operating a phacoemulsification system which includes a phacoemulsification handpiece, and an ultrasonic power source, a vacuum source, a source of irrigating fluid, and a control unit having a vacuum sensor for controlling the aspiration of the irrigating fluid from the handpiece. The method includes the steps of placing the handpiece in an operative relationship with an eye for phacoemulsification procedure and supplying irrigation fluid from the irrigation fluid source into the eye.

Pulsed ultrasonic power is provided from the ultrasonic power source to the handpiece for performing the phacoemulsification procedure. Preferably the pulsed power of a duration of less than 20 milliseconds or at a repetition rate of between 25 and about 2000 pulses per second.

A vacuum is applied from the vacuum source to the handpiece to aspirate the irrigating fluid from the eye through the handpiece at a selected rate.

An input is provided enabling manual selection of power pulse amplitude.

A voltage current phase relationship of the power from the power source may be determined and in response thereto, the ultrasonic power being provided to the handpiece is variably controlled.

In one embodiment of the present invention, the variable control of the power includes varying the pulse duty cycle of the supply power in response to the pulse amplitude and/or voltage current phase relationship.

BRIEF DESCRIPTION OF THE DRAWINGS

The advantages and features of the present invention will be better understood by the following description when considered in conjunction with the accompanying drawings in which.

DETAILED DESCRIPTION OF THE DRAWINGS

Figure 1:
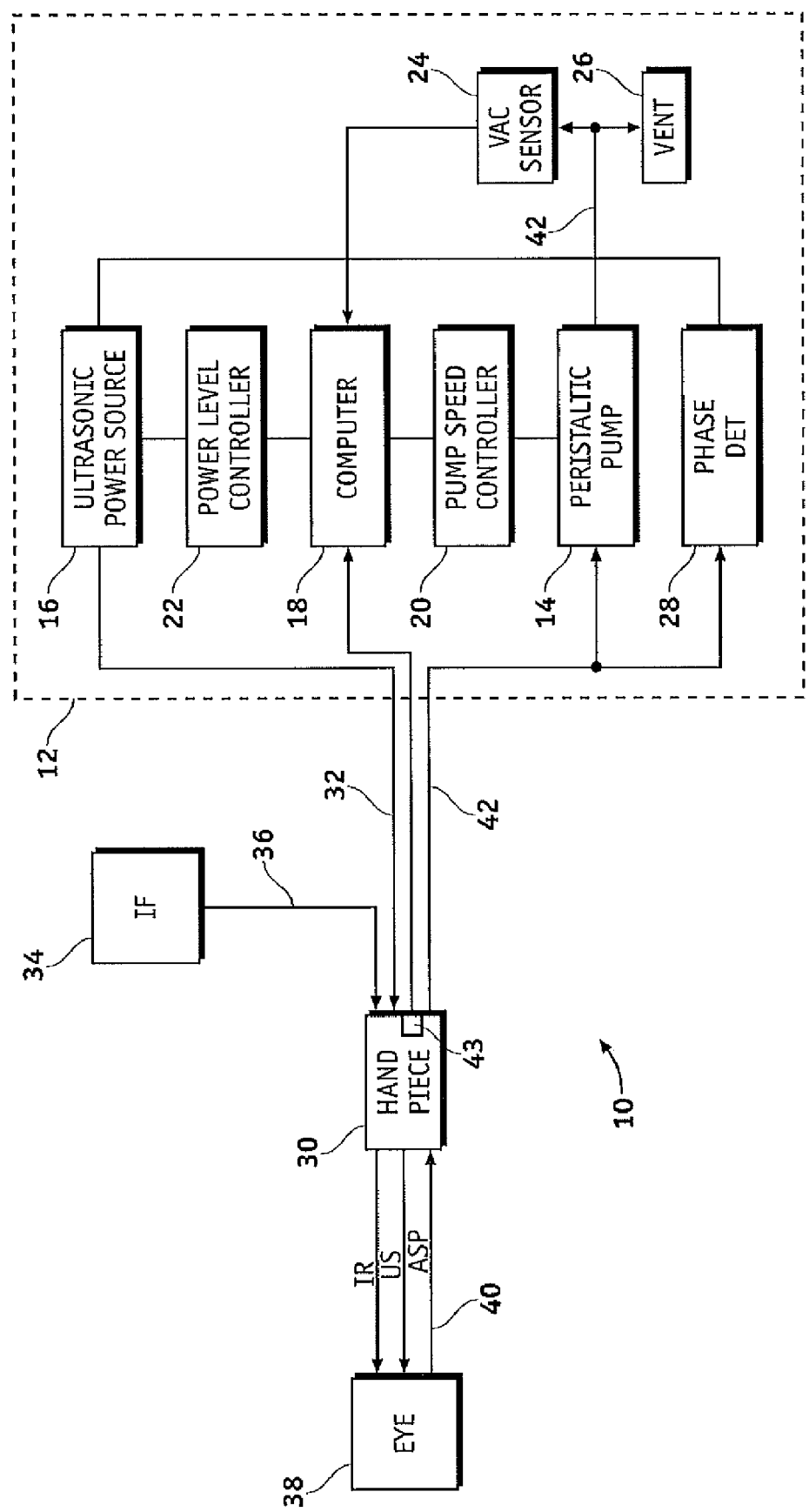
FIG. 1 is a functional block diagram of a phacoemulsification system in accordance with the present invention.

Turning now to the drawings, and particularly to FIG. 1 thereof, there is shown, in functional block diagram form, a phacoemulsification system indicated generally by the reference numeral 10. The system has a control unit 12, indicated by the dashed lines in FIG. 1 which includes a variable speed peristaltic pump 14, which provides a vacuum source, a source of pulsed ultrasonic power 16, and a microprocessor computer 18 that provides control outputs to pump speed controller 20 and ultrasonic power level controller 22. A vacuum sensor 24 provides an input to computer 18 representing the vacuum level on the output side of peristaltic pump 14. Suitable venting is provided by vent 26.

As hereinafter described in greater detail, a phase detector 28 provides an input to computer 18 representing a phase shift between a sine wave representation of the voltage applied to a handpiece/needle 30 and the resultant current into the handpiece 30. The block representation of the handle 30 includes a typical handpiece having a needle and electrical means, typically a piezoelectric crystal, for ultrasonically vibrating the needle.

The control unit 12 supplied ultrasonic power on line 32 to a phacoemulsification handpiece/needle 30. An irrigation fluid source 34 is fluidly coupled to handpiece/needle 30 through line 36. The irrigation fluid and ultrasonic power are applied by handpiece/needle 30 to a patient's eye which is indicated diagrammatically by block 38. Aspiration of the eye 38 is achieved by means of the control unit peristaltic pump 14 through lines 40 and 42. A switch 43 disposed on the handpiece 30 may be utilized as a means for enabling a surgeon to select an amplitude of electrical pulses to the handpiece via the computer 18, power level controller 22 and ultrasonic power source 16 as hereinafter discussed. It should be appreciated that any suitable input means, such as, for example, a foot pedal (not shown) may be utilized in lieu of the switch 43.

The computer 18 responds to preset vacuum levels in output line 42 from peristaltic pump 14 by means of signals from the previously mentioned vacuum sensor 24. Operation of the control unit in response to the occluded-unoccluded condition of handpiece 30 is shown in the flow diagram of FIG. 3.

Figure 3:
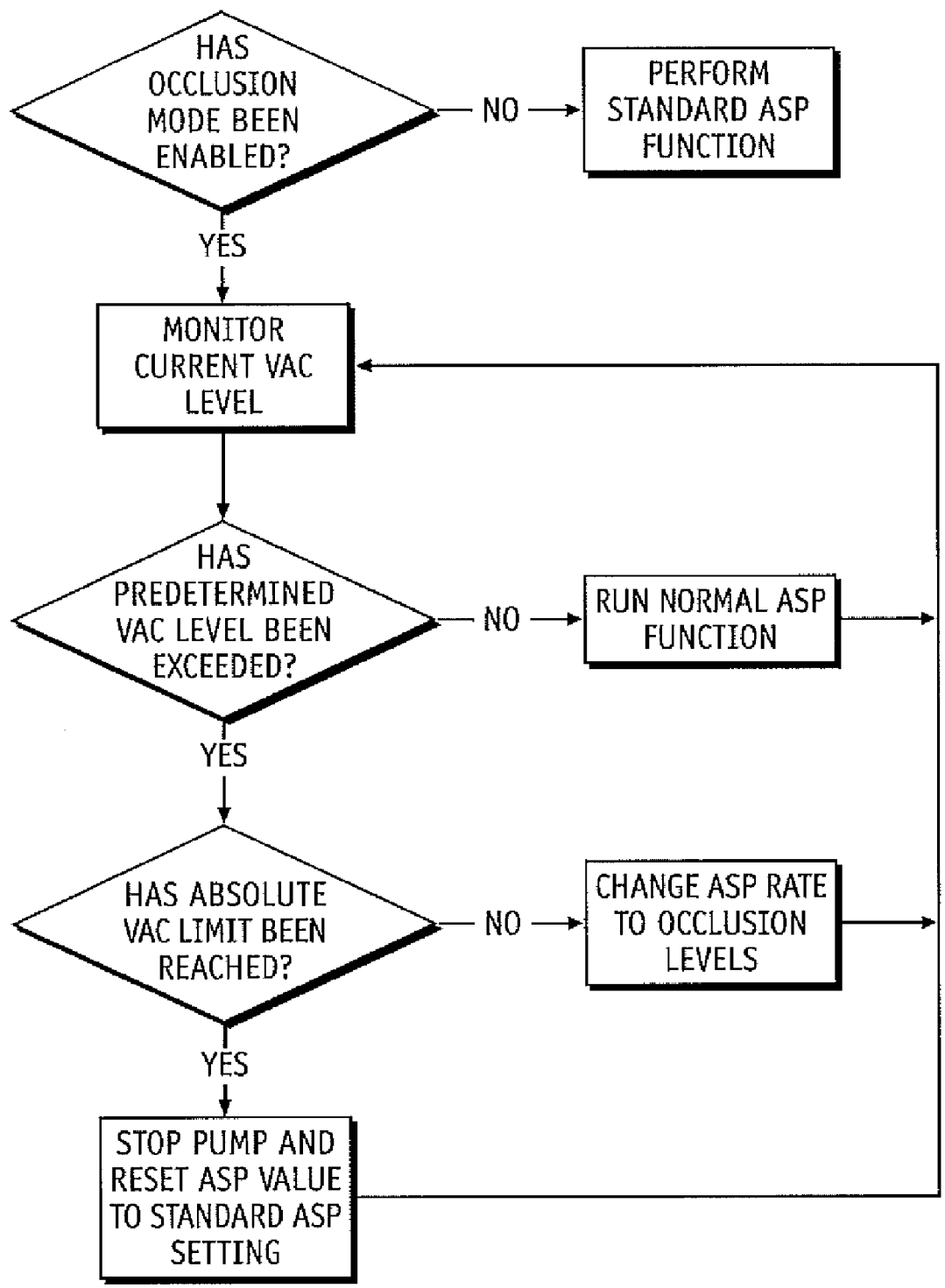
FIG. 3 is a flow chart illustrating the operation of the occluded-unoccluded mode of the phacoemulsification system with variable aspiration rates.

As shown in FIG. 3, if the handpiece aspiration line 40 is occluded, the vacuum level sensed by vacuum sensor 24 will increase. The computer 18 has operator-settable limits for aspiration rates, vacuum levels and ultrasonic power levels. As illustrated in FIG. 3, when the vacuum level sensed by vacuum sensor 24 reaches a predetermined level as a result of occlusion of the handpiece aspiration line 40, computer 18 instructs pump speed controller 20 to change the speed of the peristaltic pump 14 which, in turn, changes the aspiration rate. It will be appreciated that, depending upon the characteristics of the material occluding handpiece/needle 30, the speed of the peristaltic pump 14 can either be increased or decreased. When the occluding material is broken up, the vacuum sensor 24 registers a drop in vacuum level, causing computer 18 to change the speed of peristaltic pump 14 to an unoccluded operating speed.

Figure 4:
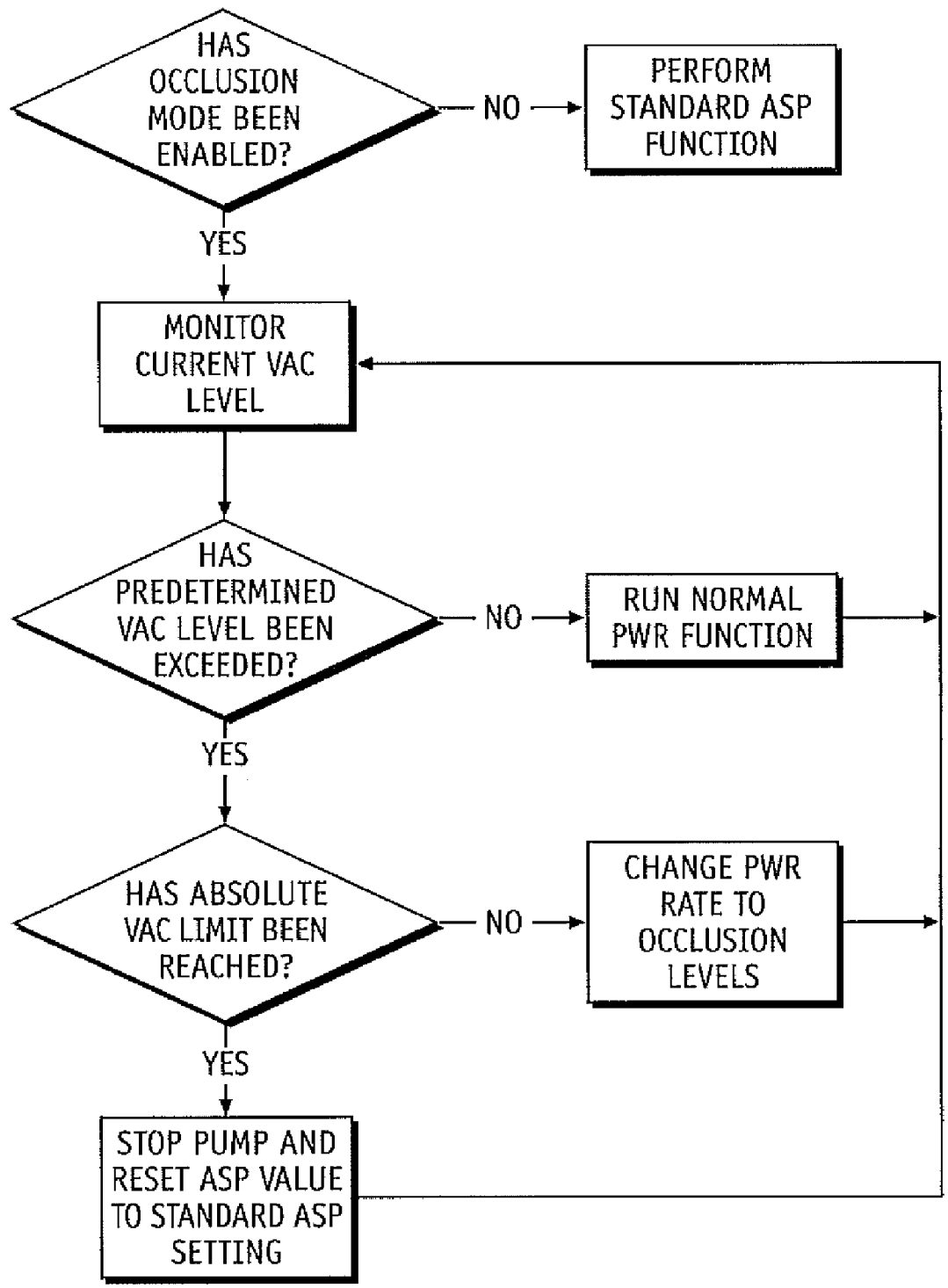
FIG. 4 is a flow chart illustrating the operation of the occluded-unoccluded mode of the phacoemulsification system with variable ultrasonic power levels.

In addition to changing the phacoemulsification parameter of aspiration rate by varying the speed of the peristaltic pump 14, the power level of the ultrasonic power source 16 can be varied as a function of the occluded or unoccluded condition of handpiece 30. FIG. 4 illustrates in flow diagram form the control of the ultrasonic power source power level by means of computer 18 and power level controller 22. It will be appreciated that the flow diagram of FIG. 4 corresponds to the flow diagram of FIG. 3 but varies the phacoemulsification parameter of the ultrasonic power level.

Figure 5:
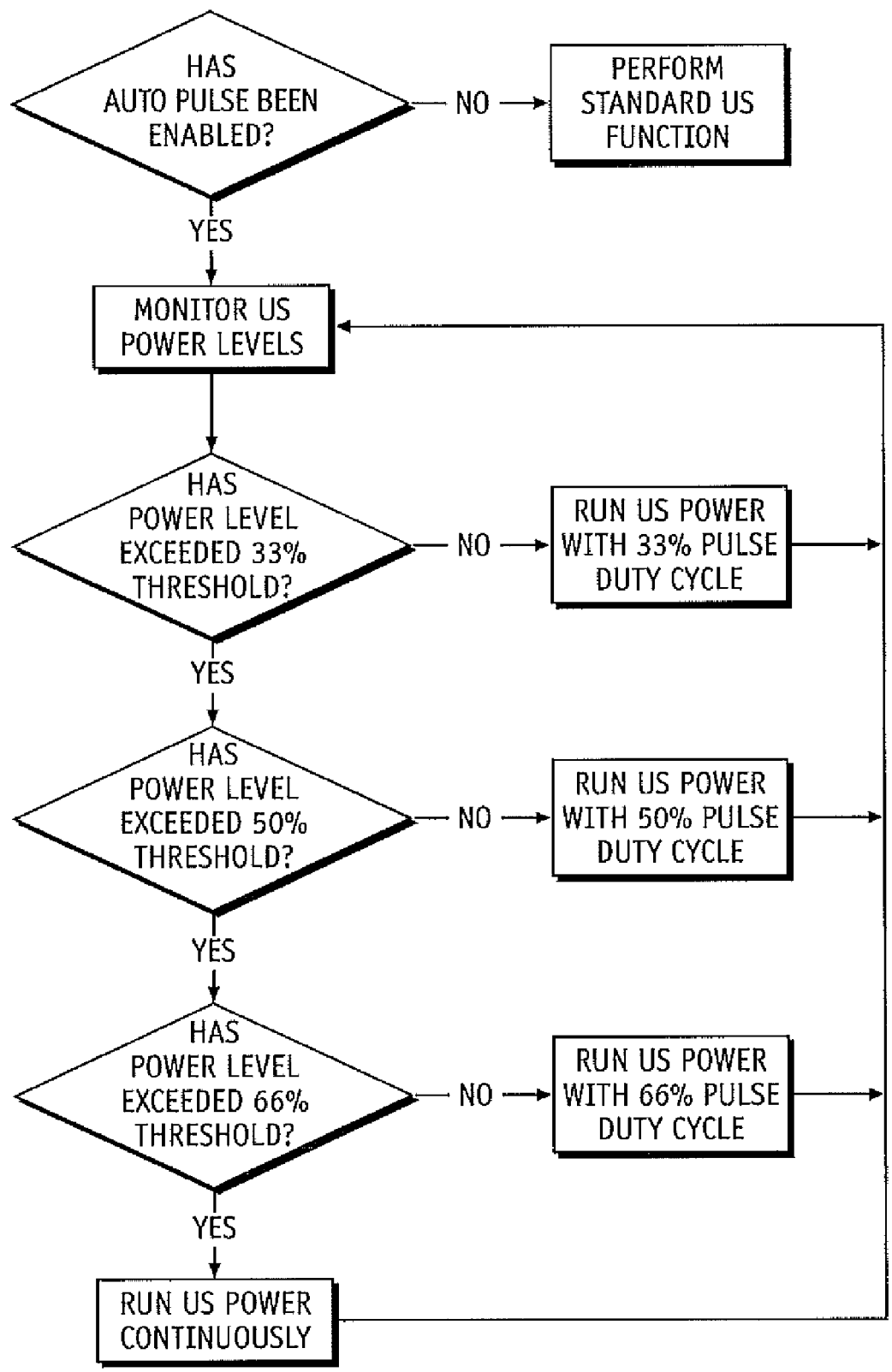
FIG. 5 is a flow chart illustrating the operation of a variable duty cycle pulse function of the phacoemulsification system.

With reference to FIG. 5, there is shown a flow diagram depicting the control of the ultrasonic power source 16 to produce varying pulse duty cycles as a function of selected power levels. Each power pulse may have a duration of less than 20 milliseconds. As shown in FIG. 5, and by way of illustration only, a 33% pulse duty cycle is run until the power level exceeds a preset threshold; in this case, 33%. At that point, the pulse duty cycle is increased to 50% until the ultrasonic power level exceeds a 50% threshold, at which point the pulse duty cycle is increased to 66%. When the ultrasonic power level exceeds 66% threshold, the power source is run continuously, i.e., a 100% duty cycle. Although the percentages of 33, 50 and 66 have been illustrated in FIG. 5, it should be understood that other percentage levels can be selected as well as various duty cycles to define different duty cycle shift points. Importantly, the pulse duration may be less than 20 milliseconds. This advanced control along with the tracking mechanism herein described enables bursts of energy less than 20 milliseconds in duration. This control is effective in providing rapid pulse phaco power for burn free surgery.

Figure 13:
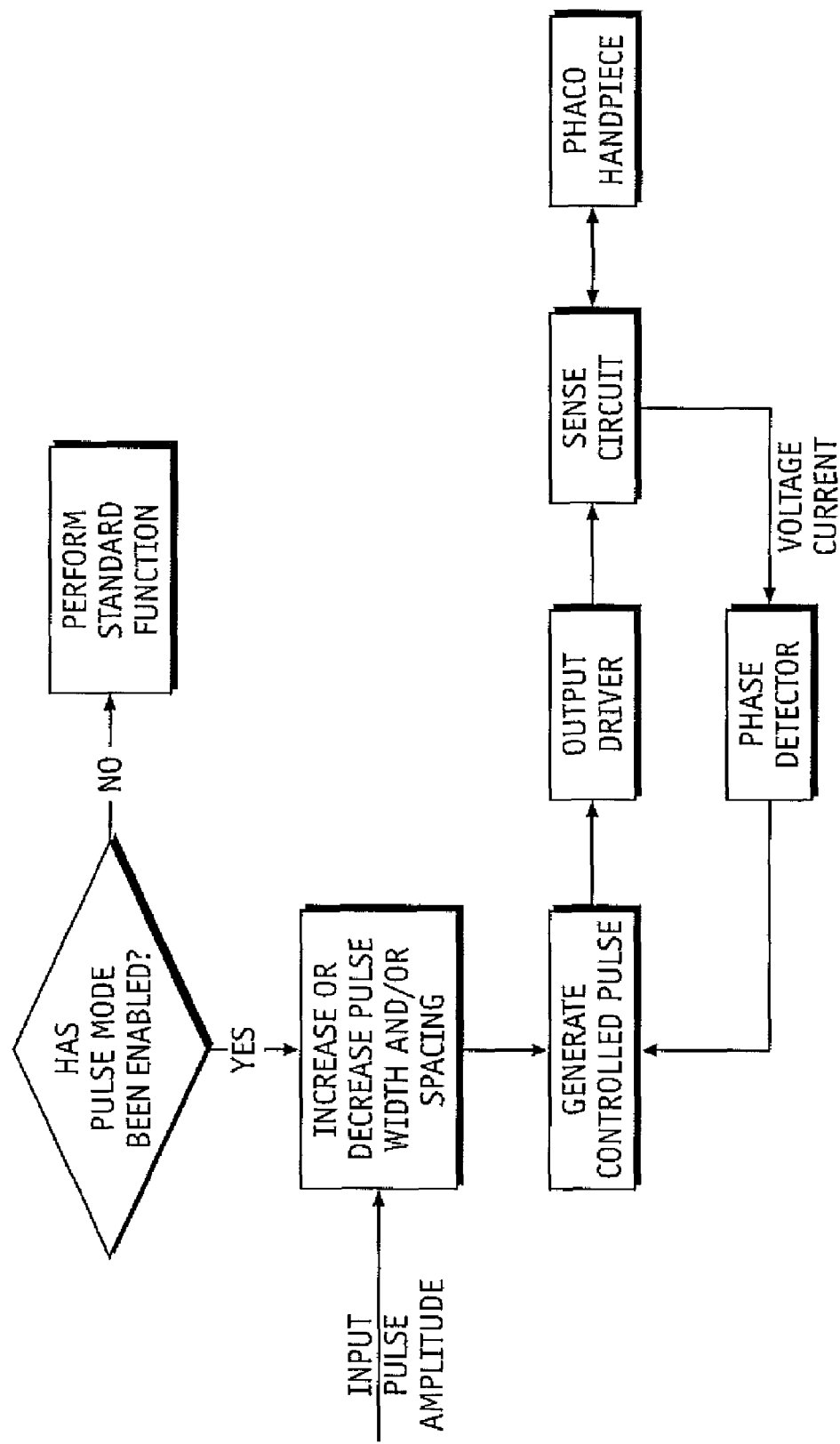
FIG. 13 is a function block control diagram of a pulse control phacoemulsification system.

With reference to FIG. 13, when the computer 18 has been enabled for pulse mode operation via the switch 43, the use of thermal tissue damage is reduced. In accordance with the present invention, very rapid pulse duration of less than 20 milliseconds is provided with adequate energy to cut the tissue with kinetic or mechanical energy but then the pulse is turned off long enough to eliminate the thermal BTU's before the next pulse is activated.

A surgeon may vary the pulse amplitude in a linear manner via the switch 43 and the control unit in response to the selected pulse amplitude, irrigation and aspiration fluid flow rates, controlling a pulse duty cycle. As hereinabove noted, an off duty duration or cycle is provided to ensure heat dissipation before a subsequent pulse is activated. In this way, increase amplitude will increase tip acceleration and thus BTU's for tissue damaging heat generation. That is, the surgeon can use linear power control to select the correct acceleration necessary to cut through the tissue density while the control unit provides a corresponding variation in pulse width of less than 20 milliseconds and "Off time" to prevent tissue de-compensation from heat. The control unit is programmed depending on the phaco handpiece chosen (total wattage) or the phaco tip (dimensions, weight). This use of rapid pulsing is similar to how lasers operate with very short duration pulses. Pulses may have a repetition rate of between about 25 and 2000 pulses per second.

Figure 2:
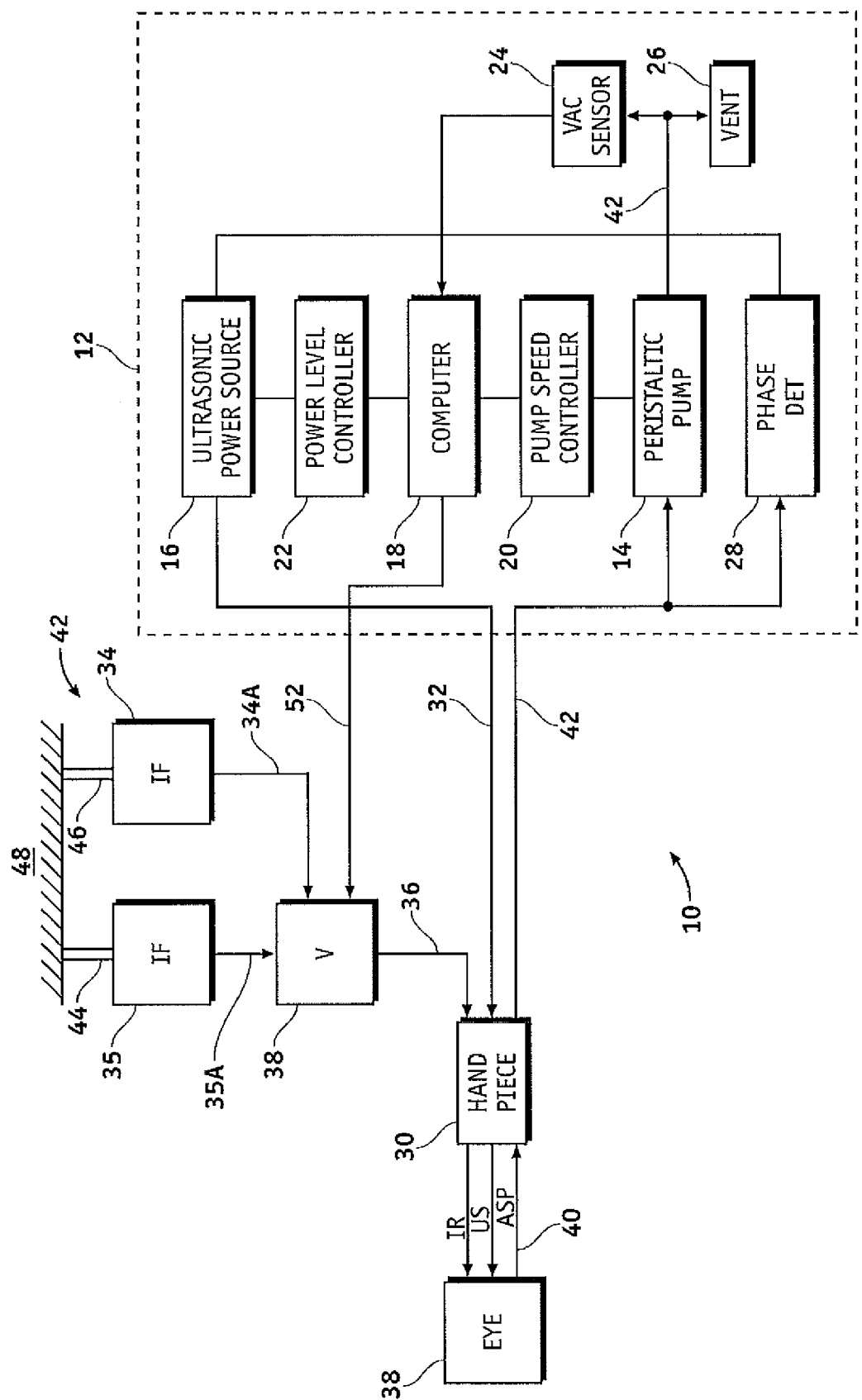
FIG. 2 is a functional block diagram of an alternative embodiment of a phacoemulsification system in accordance with the present invention which includes apparatus for providing irrigation fluid at more than one pressure to a handpiece.

Turning back to FIG. 2, there is shown an alternative embodiment 50 of a phacoemulsification system, in accordance with the present invention, and which incorporates all of the elements of the system 10 shown in FIG. 1, with identical reference characters identifying components, as shown in FIG. 1.

In addition to the irrigation fluid source 34, a second irrigation fluid source 35 is provided with the sources 34, 35 being connected to the line 36 entering the handpiece/needle 30 through lines 34a, 35a, respectively, and to a valve 38. The valve 38 functions to alternatively connect line 34a and source 34 and line 38a and source 35 with the handpiece/needle 30 in response to a signal from the power level controller 22 through a line 52.

As shown, irrigation fluid sources 34, 35 are disposed at different heights above the handpiece/needle 30 providing a means for introducing irrigation fluid to the handpiece at a plurality of pressures, the head of the fluid in the container 35 being greater than the head of fluid in the container 34. A harness 42, including lies of different lengths 44, 46, when connected to the support 48, provides a means for disposing the containers 34, 35 at different heights over the handpiece/needle 30.

The use of containers for irrigation fluids at the various heights is representative of the means for providing irrigation fluids at different pressures, and alternatively, separate pumps may be provided with, for example, separate circulation loops (not shown) which also can provide irrigation fluid at discrete pressures to the handpiece/needle 30 upon a command from the power controller 22.

With reference to FIG. 5, if the handpiece aspiration line 38 is occluded, the vacuum level sensed by the vacuum sensor 24 will increase. The computer 18 has operator-settable limits for controlling which of the irrigation fluid supplies 32, 33 will be connected to the handpiece 30. It should be appreciated that while two irrigation fluid sources, or containers 32, 33 are shown, any number of containers may be utilized.

Figure 6:
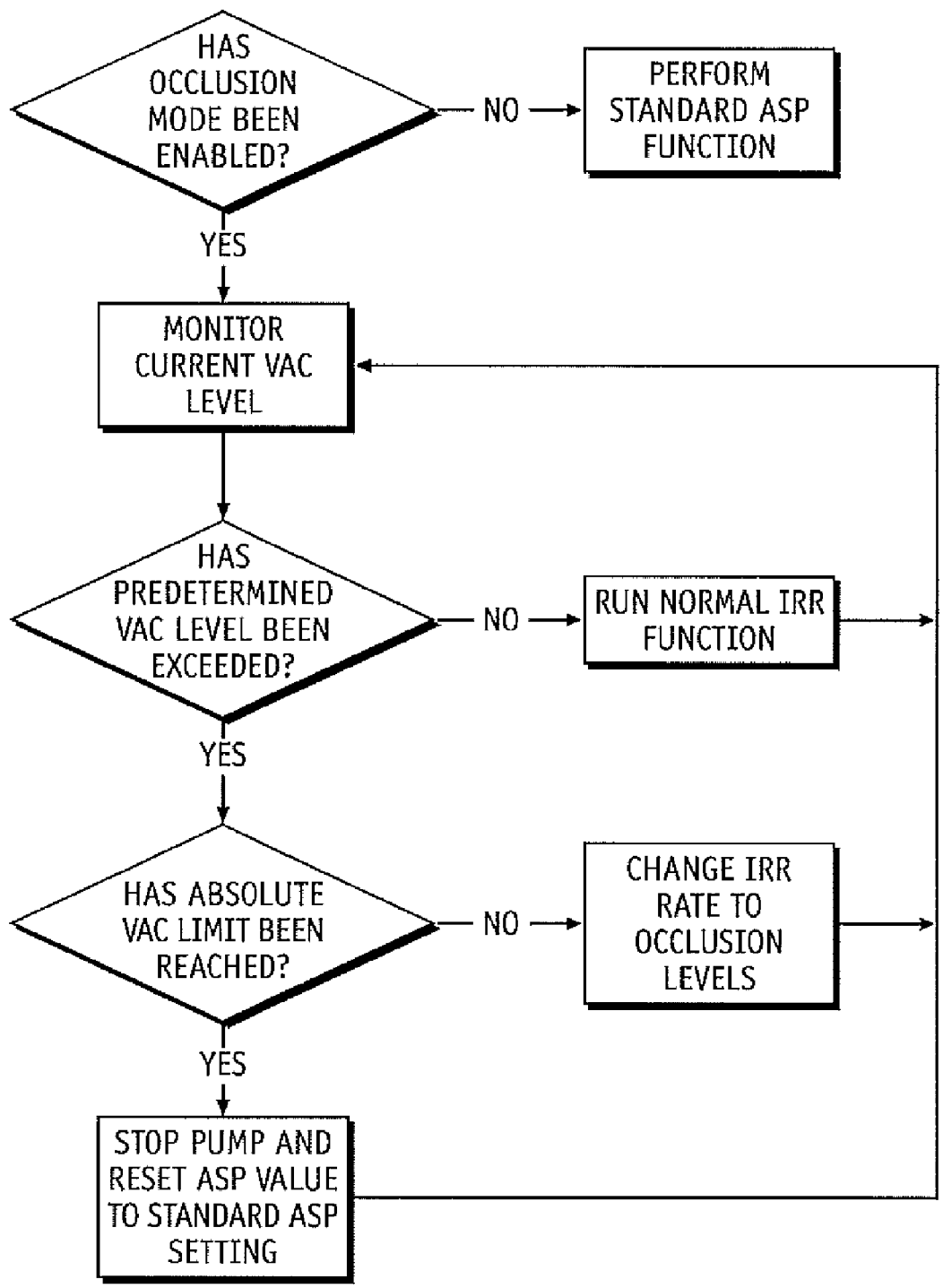
FIG. 6 is a flow chart illustrating the operation of the occluded-unoccluded mode of the phacoemulsification system with variable irrigation rates.

As shown in FIG. 6, when the vacuum level by the vacuum sensor 24 reaches a predetermined level, as a result of occlusion of the aspiration handpiece line 38, the computer controls the valve 38 causing the valve to control fluid communication between each of the containers 34, 35 and the handpiece/needle 30.

It should be appreciated that, depending upon the characteristics of the material occluding the handpiece/needle 30, as hereinabove described and the needs and techniques of the physician, the pressure of irrigation fluid provided the handpiece may be increased or decreased. As occluded material 24, the vacuum sensor 24 registers a drop in the vacuum level causing the valve 38 to switch to a container 34, 35, providing pressure at an unoccluded level.

As noted hereinabove, it should be appreciated that more than one container may be utilized in the present invention, as an additional example, three containers (not shown) with the valve interconnecting to select irrigation fluid from any of the three containers, as hereinabove described in connection with the FIG. 1A container system.

In addition to changing phacoemulsification handpiece/needle 30 parameter as a function of vacuum, the occluded or unoccluded state of the handpiece can be determined based on a change in load sensed by a handpiece/needle by way of a change in phase shift or shape of the phase curve.

Figure 7:
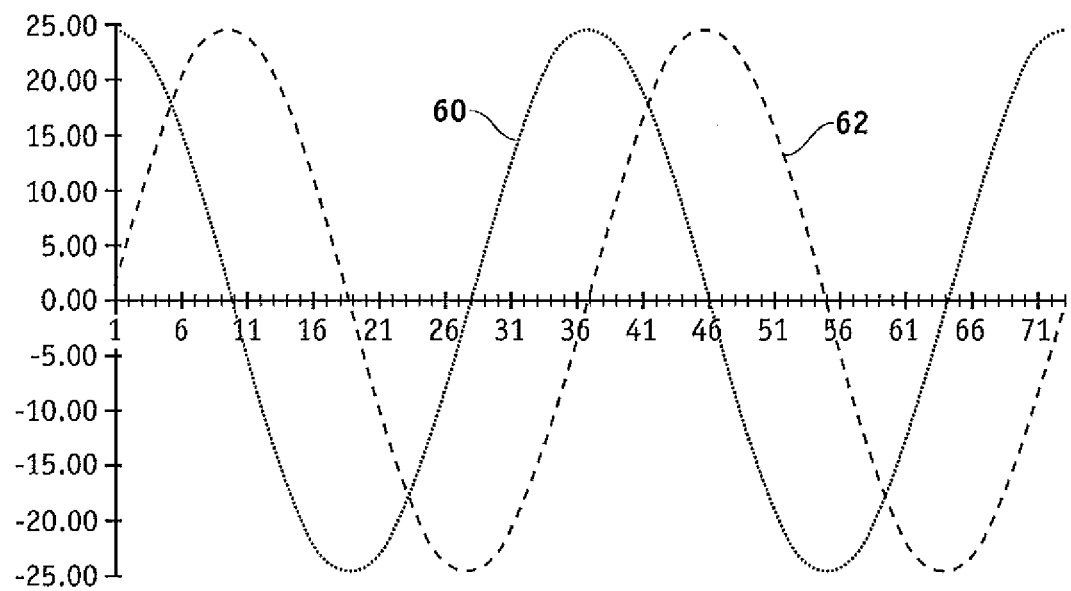
FIG. 7 is a plot of the 90 degree phase shift between the sine wave representation of the voltage applied to a piezoelectric phacoemulsification handpiece and the resultant current into the handpiece.

The typical range of frequencies used for phacoemulsification handpiece 30 is between about 30 kHz and about 50 kHz. When the frequency applied to the handpiece is significantly higher, or lower than resonancy, it responds electrically as a capacitor. The representation of this dynamic state is shown in FIG. 7 in which curve 60 (solid line) represents a sine wave corresponding to handpiece 30 current and curve 62 (broken line) represents a sine wave corresponding to handpiece 30 voltage.

Figure 8:
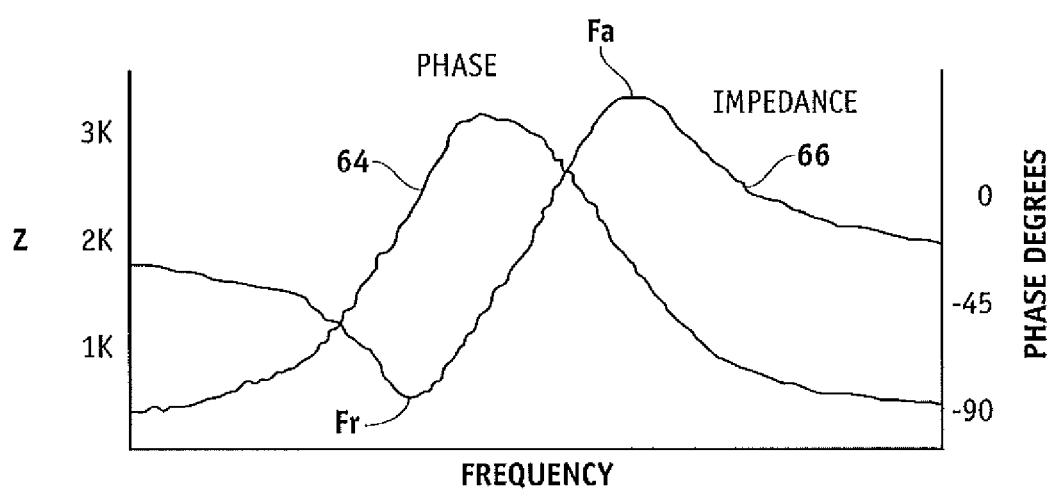
FIG. 8 is a plot of the phase relationship and the impedance of a typical piezoelectric phacoemulsification handpiece.

The impedance of the typical phacoemulsification handpiece 30 varies with frequency, i.e., it is reactive. The dependence of typical handpiece 30 phase and impedance as a function of frequency is shown in FIG. 8 in which curve 64 represents the phase difference between current and voltage of the handpieces function frequency and curve 66 shows the change in impedance of the handpiece as a function of frequency. The impedance exhibits a low at "Fr" and a high "Fa" for a typical range of frequencies.

Automatic tuning of the handpiece, as hereinabove briefly noted, is typically accomplished by monitoring the handpiece electrical signals and adjusting the frequency to maintain a consistency with selected parameters.

In order to compensate for a load occurring at the tip of the phacoemulsification handpiece, the drive voltage to the handpiece can be increased while the load is detected and then decreased when the load is removed. This phase detector is typically part of the controller in this type of system.

In such conventional phase detectors, the typical output is a voltage as proportional to the difference in alignment of the voltage and the current waveform, for example, −90 degrees as shown in FIG. 7. As shown in FIG. 8, it is important to consider that during the use of the handpiece, the waveform is varying in phase and correspondingly the output waveform is also varying.

Heretofore, the standard technique for measuring electrical phase has been to read a voltage that is proportional to phase and also to frequency. This type of circuit can be calibrated for use with a single frequency as changing the frequency would cause the calibration data to be incorrect.

This can also be seen with single frequency systems. The corrected phase value will draft due to variation in the circuit parameters.

The other typical approach is to utilize a microprocessor to compare the value of the phase detector output with that of a frequency detector and compute the true phase. This approach is fairly complex and is subject to drift of the individual circuits as well as resolution limitations.

Figure 9:
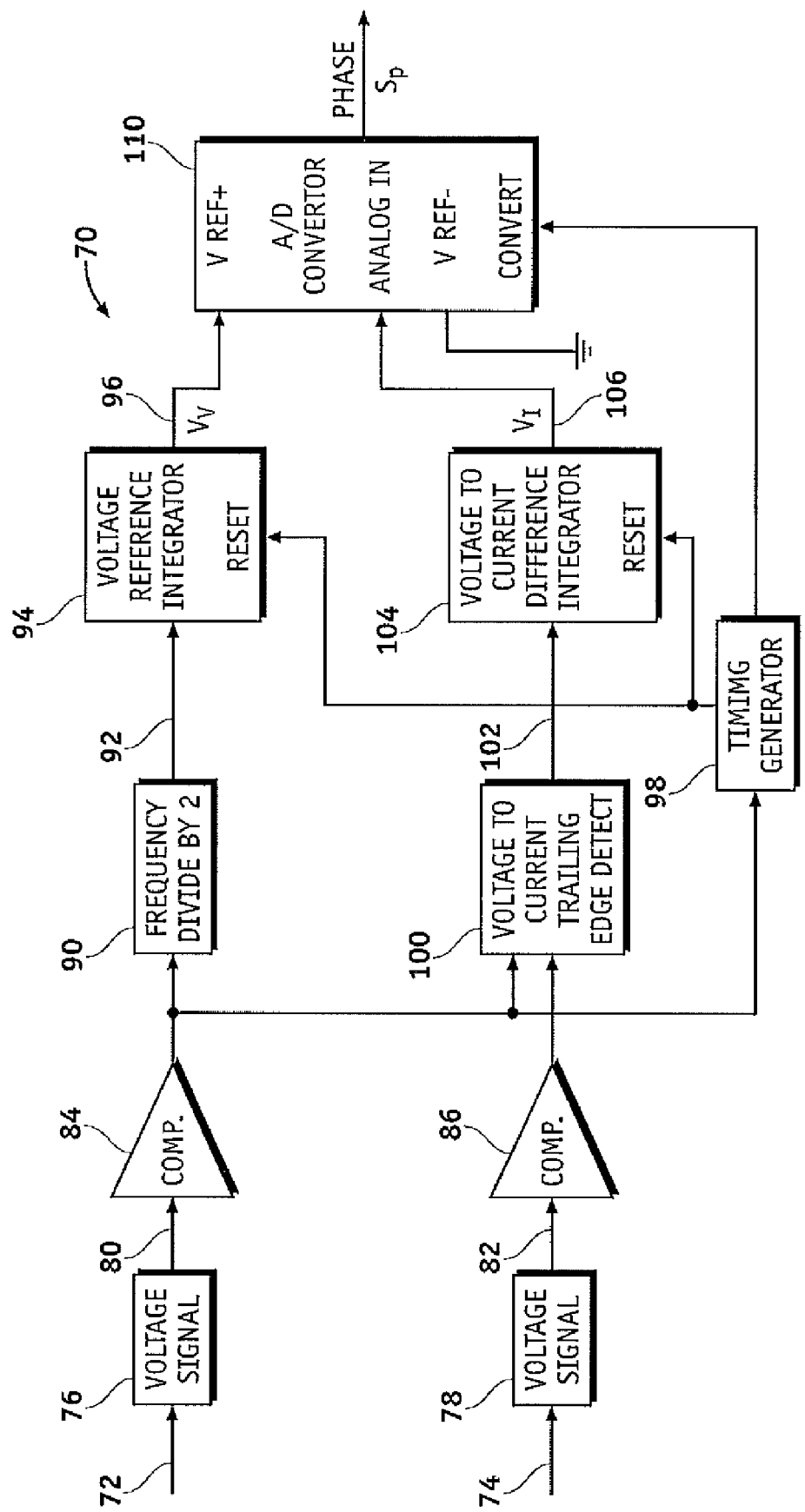
FIG. 9 is a block diagram of improved phase detector circuitry suitable for performing a method in accordance with the present invention.

A block diagram 70 as shown in FIG. 9 is representative of an improved phase detector suitable for performing the method in accordance with the present invention. Each of the function blocks shown comprises conventional state-of-the-art circuitry of typical design and components for producing the function represented by each block as hereinafter described.

The voltage input 72 and current 74 from a phacoemulsification handpiece 30 is converted to an appropriate signal using an attenuator 76 on the voltage signal to the phacoemulsification handpiece, and a current sense resistor 78 and fixed gain amplifier for the handpiece 30 current.

Thereafter, an AC voltage signal 80 and AC current signal 82 is passed to comparators 84, 86 which convert the analog representations of the phacoemulsification voltage and current to logic level clock signals.

The output from the comparator 84 is fed into a D flip flop integrated circuit 90 configured as a frequency divide by 2. The output 92 of the integrated circuit 90 is fed into an operational amplifier configured as an integrator 94. The output 96 of the integrator 94 is a sawtooth waveform of which the final amplitude is inversely proportional to the handpiece frequency. A timing generator 98 uses a clock synchronous with the voltage signal to generate A/D converter timing, as well as timing to reset the integrators at the end of each cycle.

This signal is fed into the voltage reference of an A/D converter via line 96.

The voltage leading edge to current trailing edge detector 100 uses a D flip flop integrated circuit in order to isolate the leading edge of the handpiece voltage signal. This signal is used as the initiation signal to start the timing process between the handpiece 30 voltage and handpiece 30 current.

The output 102 of the leading detector 100 is a pulse that is proportional to the time difference in occurrence of the leading edge of the handpiece 30 voltage waveform and the falling edge of the handpiece current waveform.

Another integrator circuit 104 is used for the handpiece phase signal 102 taken from the detector 100. The output 106 of the integrator circuit 104 is a sawtooth waveform in which the peak amplitude is proportional to the time difference in the onset of leading edge of the phacoemulsification voltage and the trailing edge of the onset of the handpiece current waveform. The output 106 of the integrator circuit 104 is fed into the analog input or an A/D (analog to digital converter) integrated circuit 110.

Therefore, the positive reference input 96 to the A/D converter 110 is a voltage that is inversely proportional to the frequency of operation. The phase voltage signal 96 is proportional to the phase difference between the leading edge of the voltage onset, and the trailing edge of the current onset, as well as inversely proportional to the frequency of operation. In this configuration, the two signals Frequency voltage reference 96 and phase voltage 46 track each other over the range of frequencies, so that the output of the A/D converter 110 produces the phase independent of the frequency of operation.

The advantage of utilizing this approach is that the system computer 18 (see FIGS. 1 and 2) is provided with a real time digital phase signal that 0 to 255 counts will consistently represent 0 to 359 degrees of phase.

The significant advantage is that no form of calibration is necessary since the measurements are consistent despite the frequencies utilized.

For example, using AMPs operation frequencies of 38 kHz and 47 kHz and integrator having a rise time of $150 \times 10.\sup.3 V/2$ and an 8 bit A/D converter having 256 counts, a constant ratio is maintained and variation in frequency does not affect the results. This is shown in the following examples.

EXAMPLE 1

38 KHz Operation

Period of 1 clock cycle=$1/F@38$ KHz=$26.32 \times 10^{-6}$S

Portion of one period for I=90 degrees=$26.32 \times 10^{-6}$S/$4=6.59 \times 10^{-6}$S Integrator output for one reference cycle=$(150 \times 10^{-3}$ V/S$) \times (26.32 \times 10^{-6}$S$)=3.95$ Volts Integrator output from 90 degree cycle duration=$(150) \times 10^{-3}$ V/S$) \times (6.5 \times 10^{-6}$ S$)=0.988$ Volts Resulting Numerical count from A/D converter=3.95 Volts/256 counts=0.0154 Volts per count Actual Number of A/C counts for 90 degrees at 38 KHz

EXAMPLE 2

47 KHz Operation

Period of 1 clock cycle−$1/F@47$ KHz=$21.28 \times 10^{-6}$S

Figure 10:
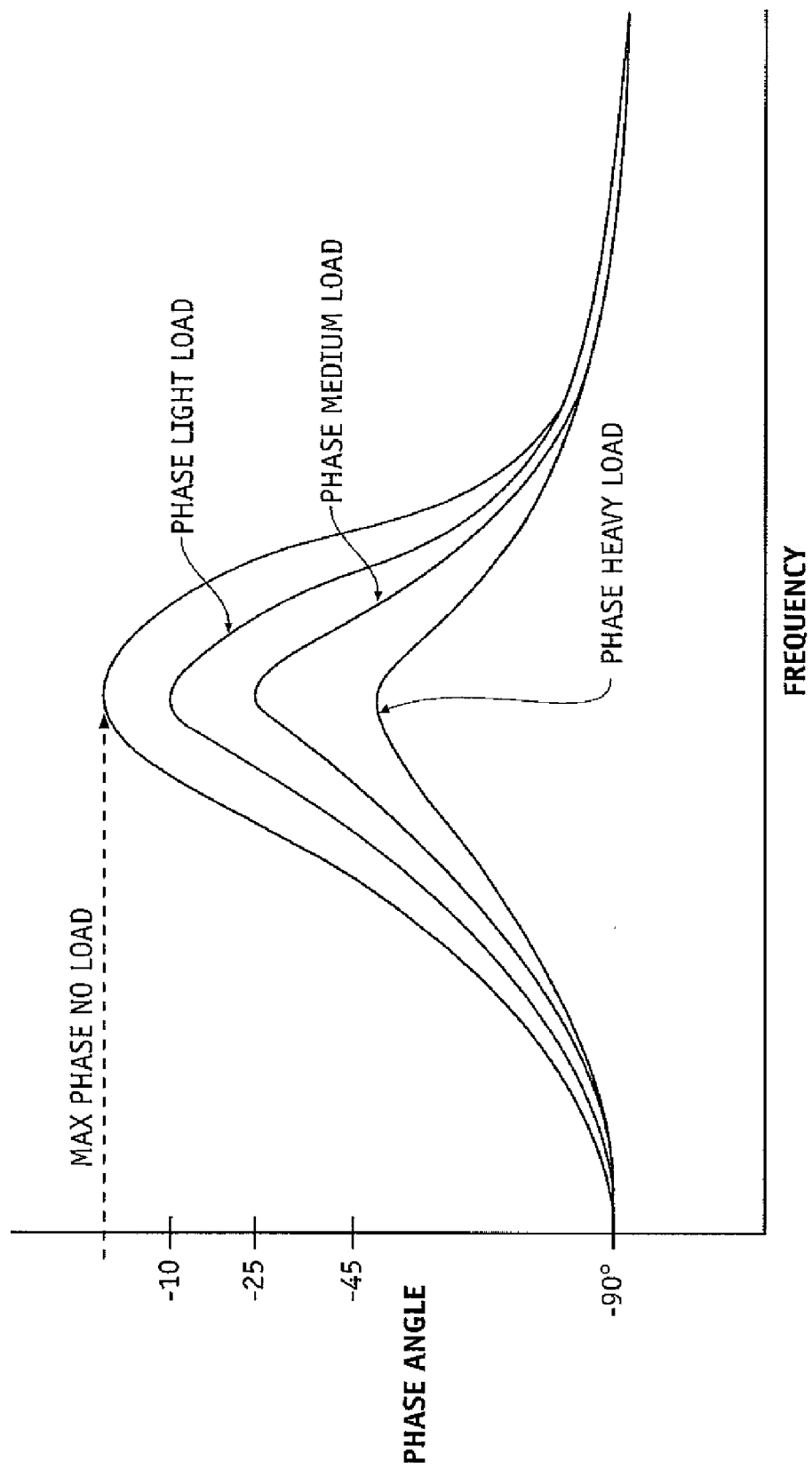
FIG. 10 is a plot of phase relationship as a function of frequency for various handpiece/needle loading.

Integrator output for one reference cycle=$(150 \times 10^3$ V/S$) \times (21.28 \times 10^{-6}$ S$)=3.19$ Volts Integrator output from 90 degree cycle duration=$(150 \times 10^3$ V/S$) \times (5.32 \times 10^{-6}$ S$)=0.798$ Volts Resulting Numerical count from A/D converter=3.19 Volts/256 counts=0.0124 Volts per count Actual Number of A/D counts for 90 degrees at 47 KHz=0.798/0.0124=64 counts A plot of phase angle as a function of frequency is shown in FIG. 10 for various handpiece 30 loading, a no load (max phase), light load, medium load and heavy load.

Figure 11:
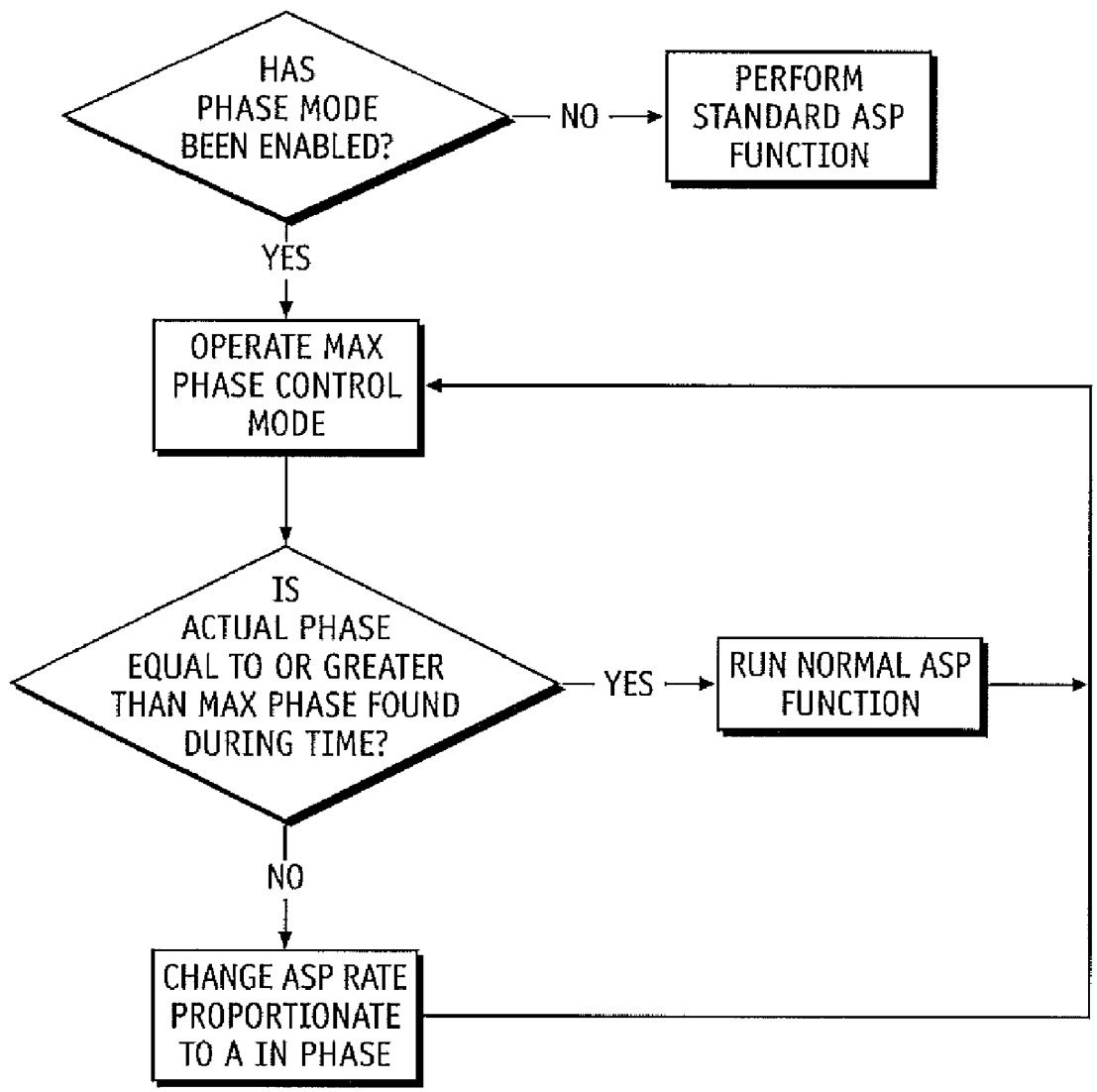
FIG. 11 is a function block diagram of a phase control phacoemulsification system utilizing phase angles to control handpiece/needle parameters with max phase mode operation.

With reference to FIG. 11, representing max phase mode operation, the actual phase is determined and compared to the max phase. If the actual phase is equal to, or greater than, the max phase, normal aspiration function is performed. If the actual phase is less than the max phase, the aspiration rate is changed, with the change being proportionate to the change in phase.

Figure 12:
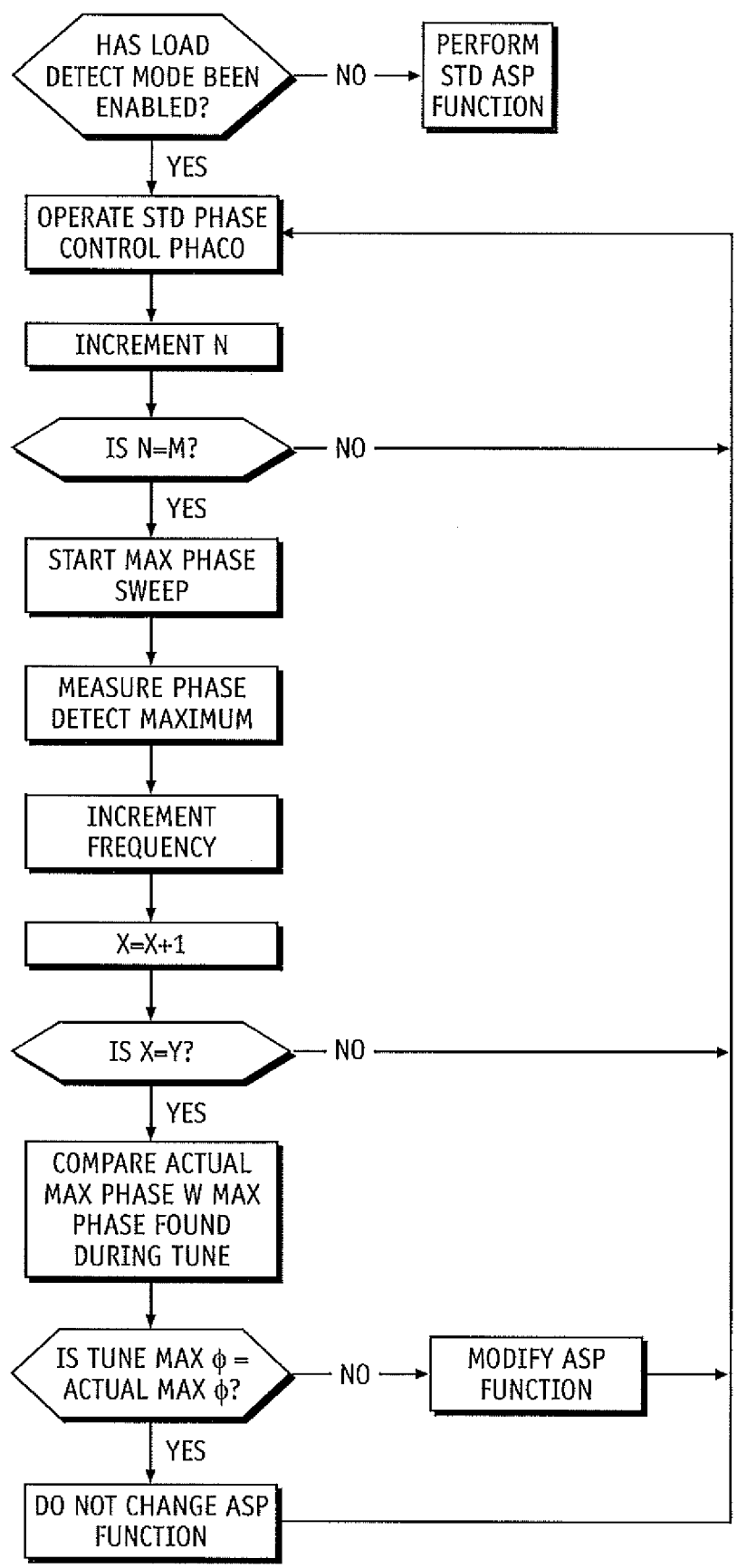
FIG. 12 is a function block control diagram of a phase control phacoemulsification system utilizing phase angles to control handpiece/needle parameters with a load detect method.

FIG. 12 represents operation at less than max load in which load (see FIG. 10) detection is incorporated into the operation, a method of the present invention.

As represented in FIG. 11, representing max phase mode operation, if the handpiece aspiration line 40 is occluded, the phase sensed by phase detector sensor 28 will decrease (see FIG. 10). The computer 18 has operator-settable limits for aspiration rates, vacuum levels and ultrasonic power levels. As illustrated in FIG. 11, when the phase sensed by phase detector 28 reaches a predetermined level as a result of occlusion of the handpiece aspiration line 40, computer 18 instructs pump speed controller 20 to change the speed of the peristaltic pump 14 which, in turn, changes the aspiration rate.

It will be appreciated that, depending upon the characteristics of the material occluding handpiece/needle 30, the speed of the peristaltic pump 14 can either be increased or decreased. When the occluding material is broken up, the phase detector 28 registers an increase in phase angle, causing computer 18 to change the speed of peristaltic pump 14 to an unoccluded operating speed.

In addition to changing the phacoemulsification parameter of aspiration rate by varying the speed of the peristaltic pump 14, the power level and/or duty cycle of the ultrasonic power source 16 can be varied as a function of the occluded or unoccluded condition of handpiece 30 as hereinabove described.

Although there has been hereinabove described a method and apparatus for controlling a phacoemulsification handpiece utilizing the voltage current phase relationship of the piezoelectric phacoemulsification handpiece in accordance with the present invention, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

The invention claimed is:

1. A method for controlling a phacoemulsification system, the system including a handpiece, ultrasonic power source, a vacuum source, a source of irrigating fluid, and a control unit, the method comprising:
   a) activating a phase mode control on the phacoemulsification system;
   b) determining an actual phase by a phase detector sensor;
   c) comparing said actual phase to a maximum phase; and
   d) changing an aspiration rate of the phacoemulsification system when the actual phase is less than the maximum phase, and maintaining normal aspiration function when the actual phase is greater than or equal to the maximum phase.

2. The method of claim 1, further comprising in between steps c) and d), determining the change between the maximum phase and the actual phase.

3. The method of claim 2, wherein the change in aspiration rate is proportional to the change between the maximum phase and the actual phase.

4. The method of claim 1, wherein the change in aspiration rate is achieved by varying the speed of a peristaltic pump.

5. The method of claim 1, further comprising in between steps a) and b), setting predetermined limits for aspiration, vacuum, and ultrasonic power.

6. The method of claim 1, wherein the control unit comprises a computer and a pump speed controller, and wherein the computer is configured to instruct the pump speed controller to change the aspiration rate.

* * * * *